United States Patent
Mahmoud et al.

(10) Patent No.: US 12,360,098 B2
(45) Date of Patent: Jul. 15, 2025

(54) ANALYTICAL DETERMINATION OF DISSOLVED GAS CONCENTRATION IN WATER PIPELINES

(71) Applicant: Saudi Arabian Oil Company, Dhahran (SA)

(72) Inventors: Mohamed Ahmed Saad Mahmoud, Dammam (SA); Ahmed Hamad Salman, Riyadh (SA); Hassan Yahiya Al-Malki, Dammam (SA)

(73) Assignee: Saudi Arabian Oil Company, Dhahran (SA)

( * ) Notice: Subject to any disclaimer, the term of this patent is extended or adjusted under 35 U.S.C. 154(b) by 300 days.

(21) Appl. No.: 17/885,377

(22) Filed: Aug. 10, 2022

(65) Prior Publication Data

US 2024/0053317 A1  Feb. 15, 2024

(51) Int. Cl.
| | |
|---|---|
| *G01N 33/18* | (2006.01) |
| *G01N 30/30* | (2006.01) |
| *G01N 30/60* | (2006.01) |
| G01N 30/02 | (2006.01) |
| G01N 30/62 | (2006.01) |
| G01N 30/88 | (2006.01) |

(52) U.S. Cl.
CPC ............ *G01N 33/18* (2013.01); *G01N 30/30* (2013.01); *G01N 30/6017* (2013.01); *G01N 30/606* (2013.01); G01N 2030/025 (2013.01); G01N 2030/3007 (2013.01); G01N 2030/626 (2013.01); G01N 2030/8804 (2013.01); G01N 2030/8872 (2013.01)

(58) Field of Classification Search
None
See application file for complete search history.

(56) References Cited

U.S. PATENT DOCUMENTS

| | | | | |
|---|---|---|---|---|
| 3,826,373 A | * | 7/1974 | Andreotti | G01N 30/20 |
| | | | | 73/864.84 |
| 4,332,769 A | | 6/1982 | Rampy et al. | |
| (Continued) | | | | |

FOREIGN PATENT DOCUMENTS

| | | | | |
|---|---|---|---|---|
| CN | 109613106 A | * | 4/2019 | G01N 1/28 |
| CN | 109100458 B | * | 10/2020 | G01N 30/24 |
| (Continued) | | | | |

OTHER PUBLICATIONS

U.S. Appl. No. 62/838,676, Mahmoud et al..

(Continued)

*Primary Examiner* — Daniel S Larkin
(74) *Attorney, Agent, or Firm* — Fish & Richardson P.C.

(57) ABSTRACT

To analytically determine concentration of dissolved gases in a water pipeline, a water sample is drawn from a source carrying water with dissolved gas, through a water source port of a four-way valve. The water sample is flowed from the water source port towards a syringe port of the valve and into a syringe fluidically coupled to the syringe port to hold the water sample. Inert gas is drawn through an inert gas port of the valve from an inert gas source and is flowed from the inert gas port towards the syringe port and into the syringe. A mixture of the water sample and the inert gas is flowed from the syringe port towards an analyzer port of the valve and into an analyzer fluidically coupled to the analyzer port.

14 Claims, 5 Drawing Sheets

(56) References Cited

U.S. PATENT DOCUMENTS

| | | | | |
|---|---|---|---|---|
| 4,384,471 | A | * | 5/1983 | Wentzel ................. G01N 30/08 |
| | | | | 422/89 |
| 4,535,620 | A | * | 8/1985 | Cunningham ......... G01N 30/88 |
| | | | | 73/23.4 |
| 10,082,489 | B2 | * | 9/2018 | Lovanni ................. B01D 15/10 |
| 2012/0272715 | A1 | * | 11/2012 | Kriel .................... G01N 33/241 |
| | | | | 73/23.42 |

FOREIGN PATENT DOCUMENTS

| | | | | |
|---|---|---|---|---|
| CS | 249044 | B1 | * | 3/1987 |
| GB | 914209 | A | * | 12/1962 ............ G01N 30/06 |
| JP | 05281217 | A | * | 10/1993 |
| JP | 09159661 | A | * | 6/1997 |
| JP | 10339690 | A | * | 12/1998 |
| JP | 11014613 | A | * | 1/1999 ............ G01N 30/10 |
| JP | 11094811 | A | * | 4/1999 |
| JP | 3404205 | B2 | * | 5/2003 |
| JP | 2013190283 | A | * | 9/2013 |
| SU | 1402926 | A1 | * | 6/1988 |

OTHER PUBLICATIONS

"Gas Chromatograph Nexis GC-2030," Shimadzu, Brochure, May 2017, 20 pages.

Åberg et al., "Evaluating a fast headspace method for measuring DIC and subsequent calculation of pCO2 in freshwater systems," Inland Waters, 2014, 4(2), 157-166, 11 pages.

Bastviken et al., "Technical Note: Cost-efficient approaches to measure carbon dioxide (CO2) fluxes and concentrations in terrestrial and aquatic environments using mini loggers," Biogeosciences, 12, 3849-3859, 2015, 11 pages.

Hope et al., "A method for measuring free CO in upland streamwater using headspace analysis," Journal of Hydrology, Mar. 1995, 166: 1-2, 1-14, 14 pages, (Abstract Only).

Kampbell, "Dissolved Oxygen and Methane in Water by a GC Headspace Equilibration Technique" International Journal of Environmental Analytical Chemistry, 1989, 36(4), 10 pages.

Pfeiffer et al., "Comparative performance of CO2 measuring methods: Marine aquaculture recirculation system application," Aquacultural Engineering, 2011 44: 1-9, 10 pages.

Sarradin et al., "Analysis of dissolved gases by headspace sampling gas chromatography with column and detector switching. Preliminary results," Analytical Communications, 33: 371-373, Oct. 1996, 3 pages.

Stainton, "A Syringe Gas-stripping Procedure for Gas-Chromatographic Determination of Dissolved Inorganic and Organic Carbon in Fresh Water and Carbonates in Sediments," Fisheries Research Board of Canada, 2011, 1973, 30(10), 5 pages (Abstract Only).

Wachowiak et al., "Distribution of Hydrogen Sulphide in Rats' Organs and Associated Histological Changes in Experimental Intoxication," Problems of Forensic Sciences, 2000, 8 pages.

SAIP Examination Report in SAIP Appln. No. 123450145, mailed on May 15, 2025, 10 pages, with English Translation.

* cited by examiner

ANALYTICAL DETERMINATION OF DISSOLVED GAS CONCENTRATION IN WATER PIPELINES

TECHNICAL FIELD

This disclosure relates to analyzing gas concentrations, e.g., gas concentrations in pipelines flowing fluids obtained during oil and gas production.

BACKGROUND

The output of hydrocarbon production includes multiple fluids including petroleum, natural gas and water. The water is flowed, e.g., through pipelines and flowlines, from one location (e.g., where the water is produced) to another location (e.g., where the water is processed). The produced water includes dissolved gases (e.g., oxygen, hydrogen sulfide, methane and carbon dioxide). Knowledge of the concentration of the dissolved gases is useful in processing the water.

SUMMARY

This specification describes technologies relating to analytical determination of dissolved gas concentration in water pipelines.

Certain aspects of the subject matter described here can be implemented as a method. A water sample is drawn from a source carrying water with dissolved gas produced during oil and gas production. The water sample is drawn through a water source port of a four-way valve fluidically coupled to the water source. The water sample is flowed from the water source port towards a syringe port and into a syringe fluidically coupled to the syringe port. The syringe is configured to hold the water sample. The water sample is flowed by avoiding an inert gas port and an analyzer port of the four-way valve. Inert gas is drawn from an inert gas source fluidically coupled to the inert gas port. The inert gas is flowed from the inert gas port towards the syringe port and into the syringe. The inert gas is flowed by avoiding the water source port and the analyzer port. A mixture of the water sample and the inert gas is flowed from the syringe port towards the analyzer port and into an analyzer fluidically coupled to the analyzer port. The mixture is flowed by avoiding the water source port and the inert gas.

An aspect combinable with any other aspect includes the following features. After flowing the mixture of the water sample and the inert gas into the analyzer, the analyzer determines a concentration of dissolved gases in the water sample using the mixture of the water sample and the inert gas.

An aspect combinable with any other aspect includes the following features. The concentration of dissolved gases is determined by determining a mole fraction of each dissolved gas.

An aspect combinable with any other aspect includes the following features. The analyzer is a gas chromatography analyzer. Before determining the concentration of dissolved gases in the water sample, the gas chromatography analyzer is calibrated.

An aspect combinable with any other aspect includes the following features. After flowing the inert gas into the syringe and before flowing the mixture of the water sample and the inert gas into the analyzer, the mixture is held in the syringe for a duration to achieve gas equilibrium of the mixture in the syringe.

An aspect combinable with any other aspect includes the following features. The duration is between 45 minutes and one hour.

An aspect combinable with any other aspect includes the following features. The water with dissolved gases flows through the source at a temperature. Before flowing the water sample into the syringe, the water sample is heated to a temperature equal to the temperature at which the water with dissolved gases flows through the source.

An aspect combinable with any other aspect includes the following features. Before flowing the water sample into the syringe, suspended solids in the water sample are filtered.

Certain aspects of the subject matter described here can be implemented as a system. The system includes a four-way valve, a controller connected to the four-way valve and an analyzer. The four-way valve includes four ports—a syringe port, a water source port, an inert gas port and an analyzer port. The syringe port is fluidically coupled to a source carrying water with dissolved gases produced during oil and gas production. The water source port is fluidically coupled to a syringe configured to hold the water sample. The inert gas port is fluidically coupled to the inert gas source. The analyzer port is fluidically coupled to the analyzer. The controller includes one or more computer systems and a computer-readable storage medium storing instructions executable by the one or more computer systems to control the four-way valve to perform operations. In response to instructions from the controller, the four-way valve draws a water sample through the water source port. The valve flows the water sample from the water source port to the syringe port while avoiding the inert gas port and the analyzer port. The water sample is flowed to the syringe. After the water sample is flowed to the syringe, the valve draws inert gas from the inert gas source through the inert gas port and flows the inert gas to the syringe port and into the syringe, while avoiding the water source port and the analyzer port. The valve flows a mixture of the water sample and the inert gas from the syringe port towards the analyzer port. The analyzer is configured to receive the mixture of the water sample and the inert gas, and to determine a concentration of dissolved gases in the water sample using the mixture of the water sample and the inert gas.

An aspect combinable with any other aspect includes the following features. The analyzer is a gas chromatography analyzer.

An aspect combinable with any other aspect includes the following features. The gas chromatography analyzer is configured to determine a mole fraction of each dissolved gas.

An aspect combinable with any other aspect includes the following features. The water with dissolved gases flows through the source at a temperature. The system includes a heater configured to heat the water sample to a temperature equal to the temperature at which the water with dissolved gases flows through the source. The system includes a filter configured to filter suspended solids in the water sample before the water sample is flowed to the syringe.

An aspect combinable with any other aspect includes the following features. The inert gas is helium. The system includes a helium tank including helium and fluidically coupled to the inert gas port.

The details of one or more implementations of the subject matter described in this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Figure 1B:
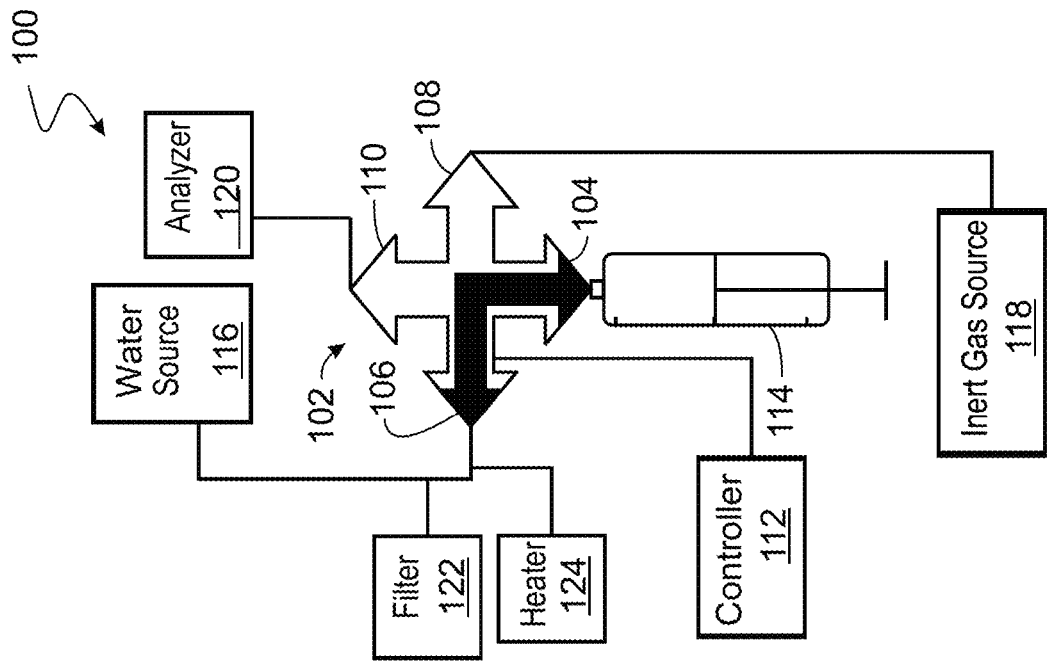
FIGS. 1A-1D are schematic diagrams of flow through a four-way valve to analyze concentration of dissolved gases in water.

This disclosure describes sample handling and test techniques to determine the concentration of dissolved gases in water. The water can be flowed in oil and gas water pipelines in, for example, water supply and water injection pipelines, utility plants and sewage treatment units. Dissolved gases can include oxygen, hydrogen sulfide, methane and carbon dioxides. Knowing the concentration of such gases can support production operations as well as preventative maintenance such as corrosion protection and plant integrity.

The techniques described here can be implemented to accurately determine the concentration of dissolved gases. The techniques are free of interference of other presented chemicals in the water pipelines, such as corrosion inhibitors and scale inhibitors in addition to oil content. The techniques can be implemented as a single method that can analyze different types of dissolved gases. Implementing the techniques described in this disclosure can reduce human error associated with test kits that use color comparators and can also reduce exposure to toxic gases like hydrogen sulfide. The selectivity of the techniques reduces interference from oil field chemicals, such as corrosion inhibitors or scale inhibitors. The techniques can reduce the amount of time needed to determine concentrations of the gases (e.g., in under 15 minutes) without any sample pre-treatment.

FIGS. 1A-1D are schematic diagrams of flow through a four-way valve to analyze concentration of dissolved gases in water. The flow system 100 shown in FIGS. 1A-1D can be implemented to analyze dissolved gases in a water sample drawn from a water source through which water with dissolved gases is flowed. For example, the water source can be a water pipeline carrying water produced during oil and gas production. Alternatively, or in addition, the water source can be a water pipeline flowing water with dissolved gases produced by utility plants or sewage water treatment units.

The flow system 100 includes a four-way valve 102 that is configured to direct flow from different sources to different destinations. The valve 102 includes four ports—a syringe port 104, a water source port 106, an inert gas port 108 and an analyzer port 110. The valve 102 includes fluid flow pathways that connect each port to every other port. The valve 102 includes mechanisms (e.g., stoppers, balls). The valve 102 can be controlled using the mechanisms. For example, the mechanisms allow flow from one port to any other port, while avoiding flow through or to the two remaining ports. The flow system 100 includes a controller 112 that includes one or more computer systems and a computer-readable medium (e.g., a non-transitory computer-readable medium) storing instructions executable by the one or more computer systems to perform certain operations. In some implementations, the controller 112 can be implemented as software, hardware, firmware, electronic circuitry or any combination of them with or without the one or more computer systems and the computer-readable medium to perform operations described here. The controller 112 is connected to the valve 102 and can control valve operations. For example, the controller 112 can transmit signals to activate or deactivate the mechanisms that are used to control the valve 102. By doing so, the controller 112 can cause the valve 1022 flow fluid between one fourth and another port, while avoiding flow through or to the two remaining ports.

In some implementations, the syringe port 104 is fluidically connected to a syringe 114. As described below, the syringe 114 can hold a water sample with dissolved gases. The water source port 106 is fluidically connected to a water source 116, which, as described earlier, can be a pipeline on a flowline through which water with dissolved gases flows. The inert gas port 108 is fluidically coupled to an inert gas source 118. For example, the inert gas source 118 is a cylinder filled with inert gas, such as helium or nitrogen. The analyzer port 110 is fluidically coupled to an analyzer 120 that is configured to receive fluids including the water sample and to determine a concentration of dissolved gases in the water sample using the received fluids. In some implementations, the analyzer 120 is a gas chromatography analyzer, which can receive fluids through the analyzer port 110, analyze the water sample for dissolved gases, and output results of the analysis as chromatograms.

Figure 1A:
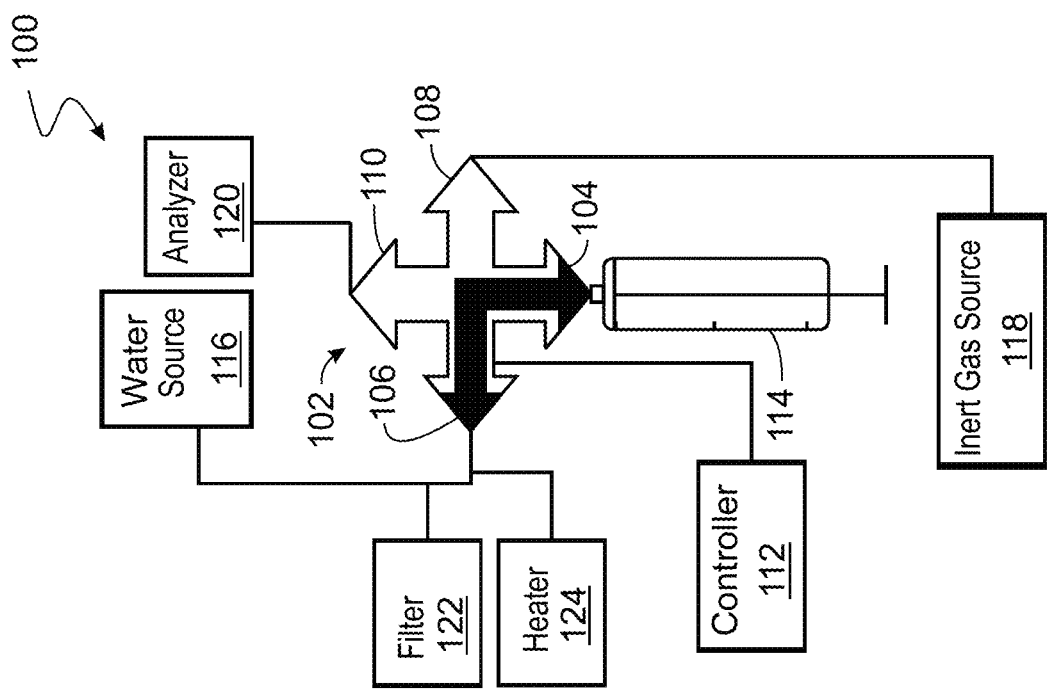

FIG. 1A shows the step of drawing the water sample through the water source port 106 from the water source 116. The water sample is flowed from the water source port 106 towards the syringe port 104 and into the syringe 114, while avoiding the inert gas port 108 and the analyzer port 110. For example, the controller 112 transmits signals to open flow between the water source port 106 and the syringe port 104, and to close flow to the inert gas port 108 and the analyzer port 110. Then, a user draws a piston in the syringe 114 causing suction in the flow pathway connecting the water source port 106 and the syringe port 104. The suction draws the water sample from the water source 116 into the syringe 114. Alternatively or in addition, the positive pressure of the water flowing through the water source 116 can be used to positively flow the water sample into the water source port 106, toward the syringe port 104 and ultimately into the syringe 114. Because flow to the inert gas port 108 and the analyzer port 110 is closed, the water sample avoids flowing to either of these ports.

In some implementations, a filter 122 is used to filter any suspended solids in the water sample drawn through the water source port 106. In some implementations, a heater 124 is implemented to heat the water sample to a temperature that is equal to a temperature at which the water flows through the water source 116. FIG. 1B shows the syringe 114 filled with the water sample. In some implementations, a volume of the water sample can equal half the volume that the syringe 114 can hold. For example, the syringe 114 can hold 100 mL, and the volume of the water sample is 50 mL.

Figure 1D:
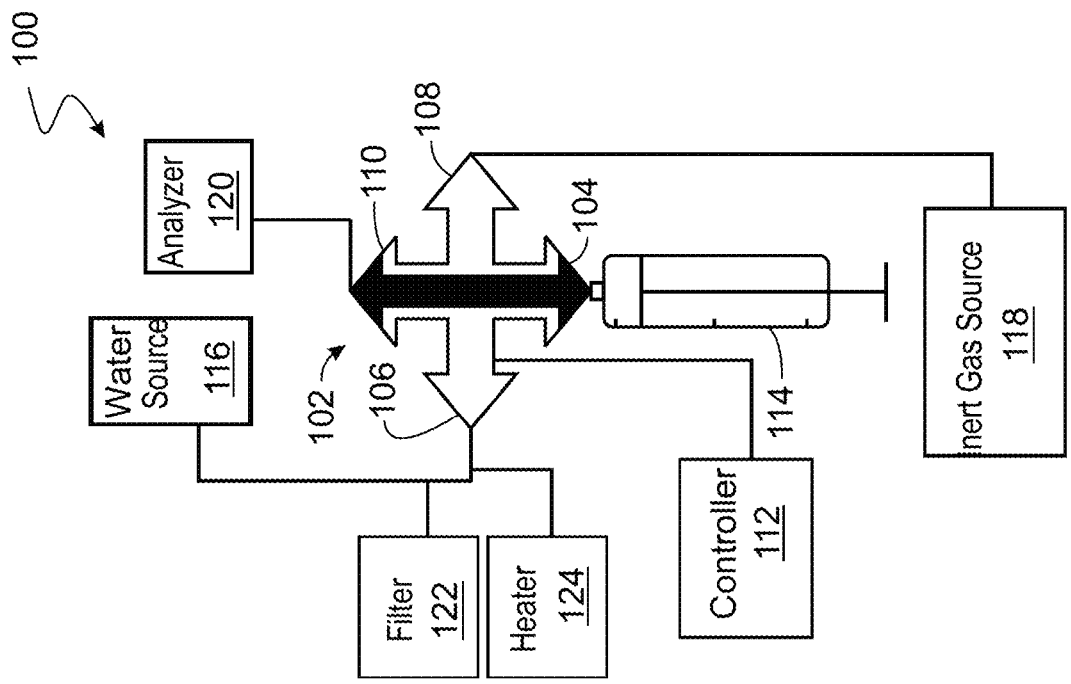
Figure 1C:
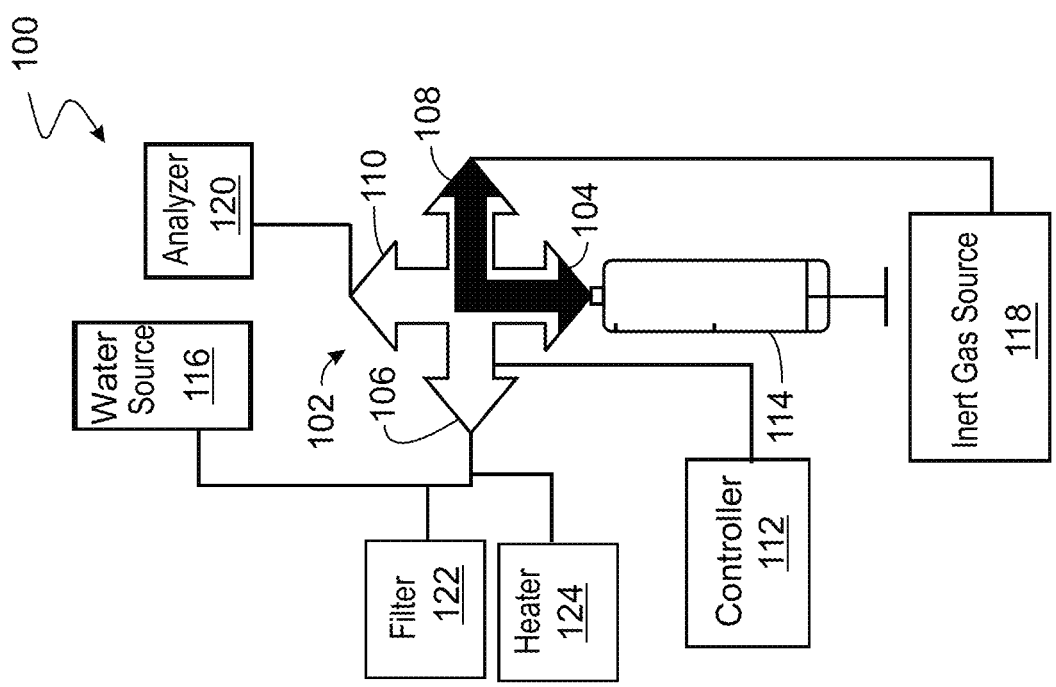

FIG. 1C shows the step of drawing inert gas through the inert gas port 108. After the water sample has been drawn into the syringe 114, the controller 112 transmits signals to open flow between the inert gas port 108 and the syringe port 104, and to close flow to the water source port 106 and the analyzer port 110. Then, the user draws the piston in the syringe 114 causing suction in the flow pathway connecting the inert gas port 108 and the syringe port 104. The suction draws the inert gas (e.g., helium, nitrogen, or other inert gas) from the inert gas source 118 into the syringe 114. In implementations in which the inert gas source 118 is a pressurized gas cylinder, the gas cylinder can be opened and the inert gas can be positively flowed from the gas cylinder into the inert gas port 108. The inert gas flows towards the syringe port 104 and into the syringe 114. Because flow to the water source port 106 and the analyzer port 110 is closed, the inert gas avoids flowing to either of these ports.

When a predetermined volume of inert gas has been drawn or flowed into the syringe 114, the inert gas flow is stopped. In some implementations, a volume of the inert gas drawn or flowed into the syringe 114 is equal to the volume of the water sample drawn into the syringe 114. For example, where the volume of the water sample is 50 mL, the volume of the inert gas is also 50 mL. After the inert gas has been flowed into the syringe 114, the mixture of the inert gas and the water sample are held in the syringe 114 for a duration to achieve gas equilibrium of the mixture in the syringe 114. For example, the controller 112 transmits signals to close the syringe port 104 to prevent leakage of the fluids in the syringe 114 back into the valve 102. The duration to achieve gas equilibrium depends on the volume of the water sample and the volume of the inert gas. For example, for a 50 mL water sample-50 mL inert gas mixture, the duration to achieve gas equilibrium is about 45 minutes.

FIG. 1D shows the step of flowing the mixture of the water sample and the inert gas from the syringe port 104 towards the analyzer port 110 and into the analyzer 120. For example, after the duration to achieve gas equilibrium has expired, the controller 112 transmits signals to open flow between the syringe port 104 and the analyzer port 110, and to close flow to the water source port 106 and the inert gas port 108. Then, the user injects a portion of the mixture of the water sample and the inert gas into the syringe port 104, towards the analyzer port 110 and into the analyzer 120. Because flow to the water source port 106 and the inert gas port 108 have been closed, the mixture avoids flowing to either of these ports.

In some implementations, the analyzer 120 (e.g., a gas chromatography analyzer) determines the concentration of dissolved gases in the water sample by determining a mole fraction of each dissolved gas. For example, the analyzer 120 can implement the following calculations for each dissolved gas.

For carbon dioxide ($CO_2$), the equilibrium between $CO_2$ present in the gas phase, $CO_2(g)$, with dissolved carbon dioxide, $CO_2(aq)$, is described by the following reaction.

$$CO_2(g) = CO_2(aq)$$

The equilibrium constant is $1/K_H$, where $K_H$ is called the Henry's law constant:

$$K_H = P_{CO2}(g) m CO_{2(aq)}$$

In the above equation, $P_{CO2}(g)$ is the partial pressure of carbon dioxide in the gas phase and $mCO_{2(aq)}$ is the molar concentration of carbon dioxide and water.

$$P_{CO2}1 = X_{CO2} P Total$$

In the above equation, X is the mole fraction of carbon dioxide.

For hydrogen sulfide ($H_2S$), the equilibrium between $H_2S$ present in the gas phase ($H_2S(g)$) with dissolved hydrogen sulfide ($H_2S(aq)$) is described by the following reaction.

$$H_2S(g) = H_2S(aq)$$

The equilibrium constant is $1/K_H$, where $K_H$ is called the Henry's law constant:

$$K_H = P_{H2S(g)} / mH_2S_{(aq)}$$

In the above equation, $P_{H2S}(g)$ is the partial pressure of hydrogen sulfide in the gas phase and $m_{H2S(aq)}$ is the molar concentration of hydrogen sulfide and water.

$$P_{H2S}1 = X_{H2S} P Total$$

In the above equation, X is the mole fraction of hydrogen sulfide.

For oxygen ($O_2$), the equilibrium between $O_2$ present in the gas phase ($O_2(g)$) with dissolved oxygen ($O_2(aq)$) is described by the following reaction.

$$O2(g) = O2(aq)$$

The equilibrium constant is $1/K_H$, where $K_H$ is called the Henry's law constant:

$$K_H = P_{O2}(g) / mO_{2(aq)}$$

In the above equation, $P_{O2}(g)$ $P_{CO2}(g)$ is the partial pressure of oxygen in the gas phase and $m_{O2}(aq)$ is the molar concentration of oxygen and water.

$$PO2\ 1 = X_{O2} P Total$$

In the above equation, X is the mole fraction of oxygen.

Similar calculations can be implemented to determine the mole fractions of other dissolved gases.

Subsequently or in parallel, Dalton's law of partial pressure of gas can be used to determine the partial pressure of each dissolved the gas in the water sample. Dalton's law of partial pressure is shown in the equation below.

$$P_{gas} = n_{gas} RT/V$$

In the Dalton's law equation, P gas represents partial pressure of a gas, V represents volume, $n_{gas}$ represents number of Moles of gas, R represents the general gas constant and T represents temperature (in Kelvin).

Henry's law is represented by the equation below.

$$C = P/K_H$$

In the Henry's law equation, C is concentration in moles and P is the partial pressure calculated from the Dalton's law equation.

In some implementations, a pressure sensor and a temperature sensor can each be coupled to the flow pathway through which the water sample is drawn into the valve 102. The total pressure (P in Henry's Law) and temperature (T in Dalton's law) can be measured using the pressure sensor than the temperature sensor, respectively. Each sensor can transmit the measured value to the controller 112.

The calculations described in this disclosure can be implemented by the controller 112 or a controller (not shown) deployed in the analyzer 120. Alternatively or in addition, the calculations described in this disclosure can be distributed between the controller 112 and the controller deployed in the analyzer 120. For example, the controller deployed in the analyzer 120 can perform all the data correlation and transfer the final concentration in parts per million (ppm) to the controller 112. Alternatively, the un-normalized concentrations of each gas type can be calculated by the controller deployed in the analyzer 120 and transferred to the controller 112, which can convert the results to ppm. Examples of concentrations and ppm values of dissolved gases in a water sample are shown in the tables below.

| $CO_2$ mole fraction | KH | partial pressure (Mole fraction × total pressure*) | C = P/KH | $CO_2$ Mol. Weight | Concentration of $CO_2$/ 100 ml % | $CO_2$ ppm |
|---|---|---|---|---|---|---|
| 0.2985 | 29.41 | 0.067136638 | 0.00228 | 44 | 0.00512 | 51.88 |

| $H_2S$ mole fraction | KH | partial pressure (Mole fraction × total pressure*) | C = P/KH | $H_2S$ Mol. Weight | Concentration of $H_2S$/ 100 ml % | $H_2S$ ppm |
|---|---|---|---|---|---|---|
| 0.02625 | 10 | 0.005902 | 0.000590 | 34.1 | 0.001553 | 17.31 |

| $O_2$ mole fraction | KH | partial pressure (Mole fraction × total pressure*) | C = P/KH | $O_2$ Mol. Weight | Concentration of $O_2$/ 100 ml % | $O_2$ ppm |
|---|---|---|---|---|---|---|
| 0.318222 | 700 | 0.0716 | 0.00010 | 15.99 | 0.000611 | 6.39 |

| $CH_4$ mole fraction | KH | partial pressure (Mole fraction × total pressure*) | C = P/KH | $CH_4$ Mol. Weight | Concentration of $CH_4$/ 100 ml % | $CH_4$ ppm |
|---|---|---|---|---|---|---|
| 0.38537 | 714 | 0.08665 | 0.00012 | 16.0 | 0.00076 | 7.58 |

In some implementations, the analyzer 120 (e.g., the gas chromatography analyzer) can be calibrated before determining the concentration of dissolved gases in the water sample. For example, the analyzer 120 can be calibrated using the National Institute of Standardization (NIST) traceable reference gas standard for the various dissolved gases including oxygen, carbon dioxide, methane, hydrogen sulfide and balanced with nitrogen or hydrocarbons. In another calibration technique, two different concentrations of all the gases can be determined to have linear calibration curves to cover all the detection limits. In a further calibration technique, the gases can be calibrated in mole percentage units.

Figure 2:
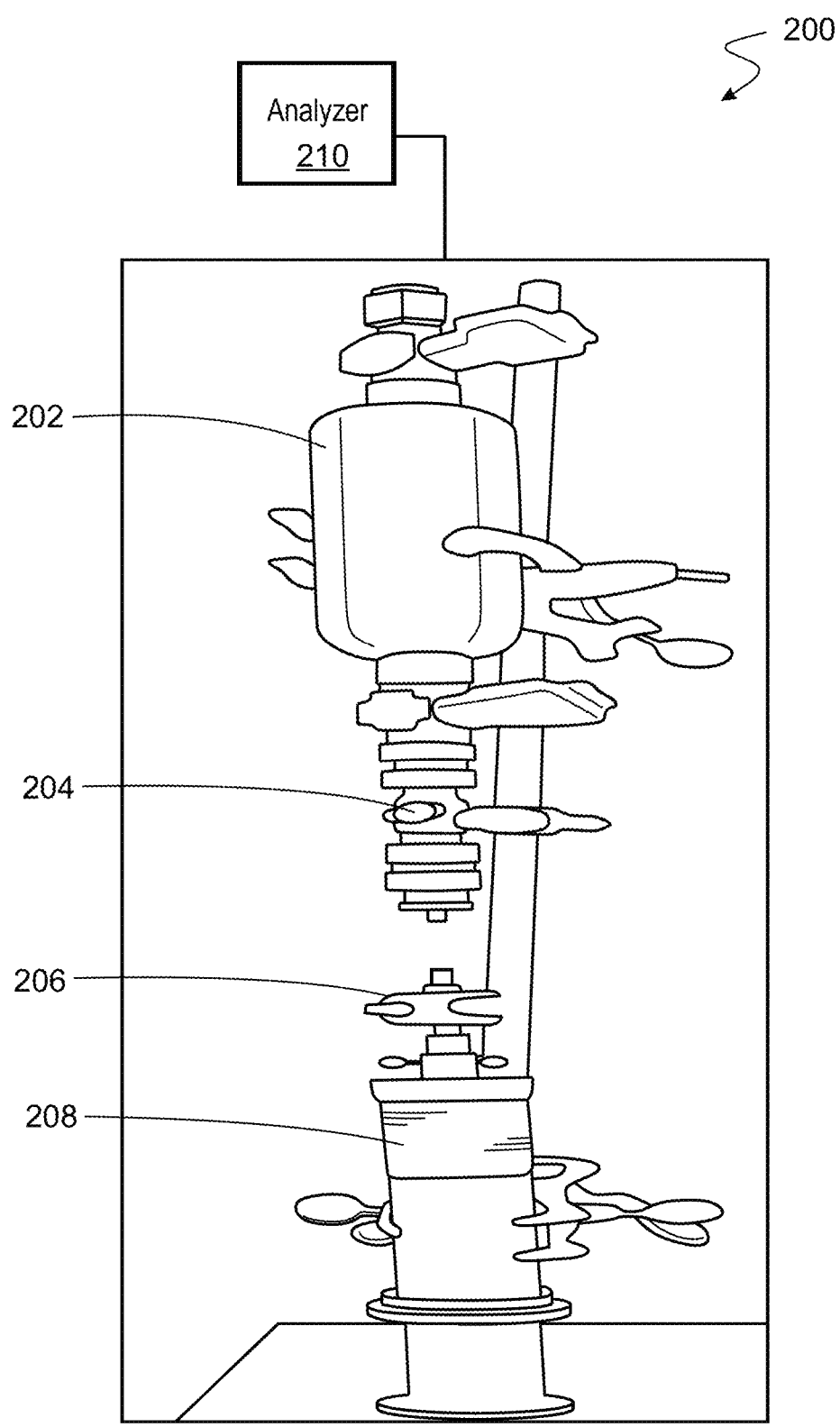
FIG. 2 is a schematic diagram of a laboratory apparatus to analyze concentration of dissolved gases in water.

FIG. 2 is a schematic diagram of a laboratory apparatus 200 to analyze concentration of dissolved gases in water. In some implementations, the techniques described with reference to FIGS. 1A-1D can be implemented using a laboratory apparatus 200 as a benchtop apparatus in a laboratory away from the water source from which the water sample is retrieved. The apparatus 200 includes an inert gas source 202, which is substantially similar to the inert gas source 118 (FIGS. 1A-1D). For example, the inert gas source 202 is a cylinder that can hold up to 200 cm 3 of helium or other inert gas. The apparatus 200 includes a metering valve 204 fluidically coupled to the inert gas source 202 to control a volume, pressure and other flow parameters of the inner gas in the inert gas source 202. The apparatus 200 includes a four-way valve 206, which is substantially similar to the valve 102 (FIGS. 1A-1D). The valve 206 is fluidically coupled to the metering valve 204 in a manner substantially similar to a fluidic coupling of the inert gas source 118 (FIGS. 1A-1D) to the inert gas port 108 (FIGS. 1A-1D). The apparatus 200 includes a syringe 208 (e.g., 100 mL interlock piston syringe), which is substantially similar to the syringe 114 (FIGS. 1A-1D). The syringe 208 is fluidically coupled to the valve 206 in a manner substantially similar to a fluidic coupling of the syringe 114 (FIGS. 1A-1D) to the syringe port 104 (FIGS. 1A-1D).

In operation, a water sample can be obtained from a water source (not shown) similar to the water source 116 (FIGS. 1A-1D). Specifically, the water sample can be drawn into the water sample carrier that can be configured to maintain the water sample at the same flow conditions (e.g., pressure, temperature, and other flow conditions) as the water in the water source from which the water sample is drawn. The water sample carrier with the water sample can be transported to the laboratory in which the apparatus 200 is implemented. Fluidic connections can be established between the water sample carrier and the valve 206. Either manually or using a controller similar to the controller 112 (FIGS. 1A-1D), operations similar to those described above with reference to FIGS. 1A-1D can be implemented on the water sample in the water sample carrier. A mixture of the water sample and the inert gas from the inert gas source 202 (after achieving gas equilibrium) can be flowed to an analyzer 210, which is substantially similar to the analyzer 120 (FIGS. 1A-1D). More fractions, concentrations and ppm of each dissolved gas in the water sample can be determined by implementing calculations similar to those described above with reference to FIGS. 1A-1D.

Figure 3:
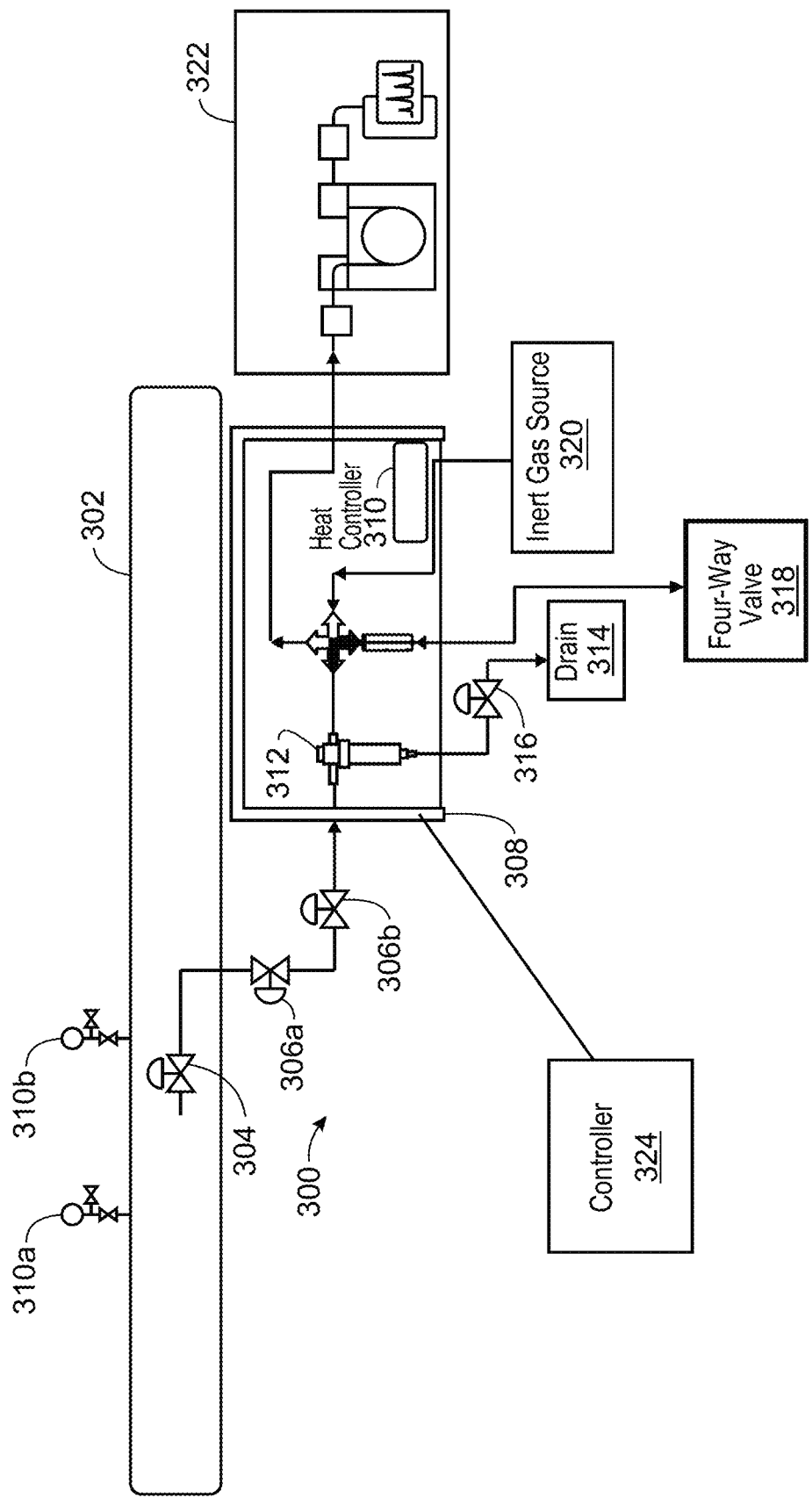
FIG. 3 is a schematic diagram of an online system to analyze concentration of dissolved gases in water.

FIG. 3 is a schematic diagram of an online system 300 to analyze the concentration of dissolved gases in water. Unlike the laboratory apparatus 200 (FIG. 2), the online system 300 can be deployed at the site of the water source 302 (e.g., a water pipeline). A water sampling system 304 can be fluidically coupled to the water source 302 (a water sample). Flow of the water sample to the online system 300 can be controlled using flow components (e.g., valves 306*a*, 306*b*). The online system 300 can be enclosed by a thermal jacket 308 that can be temperature controlled to maintain the water sample at a temperature equal to the temperature at which the water flows through the water source 302. A heat controller 310 is positioned within the terminal jacket 308 and is configured to generate heat needed to maintain the water sample at the temperature. In some implementations, temperature sensors (e.g., temperature sensors 310a, 310b) are connected to the water source 302 to measure a temperature of the water in the water source 302. The heat controller 310 is configured to receive the temperature sensed by the temperature sensors and to adjust a quantity of heat produced according to the received temperature.

In some implementations, an online filter 312 is positioned within the thermal jacket 308 and fluidically coupled to the flow components to receive the water sample from the water source 302. The online filter 312 filters any suspended solids in the water sample and flows the suspended solids to drain 314 through flow components 316. Positioned within the thermal jacket 308 is a four-way valve 318, which is substantially similar to the valve 102 (FIGS. 1A-1D). A syringe, similar to the syringe 114 (FIGS. 1A-1D) and an inert gas source 320 similar to the inert gas source 118 (FIGS. 1A-1D) fluidically coupled to the valve 318. A mixture of the water sample and inert gas (after achieving gas equilibrium) is flowed to an analyzer 322, which is substantially similar to the analyzer 120 (FIGS. 1A-1D). A controller 324, which is substantially similar to the controller 112 (FIGS. 1A-1D), is deployed to perform operations similar to those described above to determine the concentrations, more fractions and ppm values of the dissolved gas in the water sample.

The online system 300 described with reference to FIG. 3 is designed to be portable and to be deployed on the field. For example, multiple online systems 300 can each be deployed at different locations in the water source 302 to determine concentrations of dissolved gases obtained from water samples at each of those locations. By comparing the concentrations of the dissolved gases at the different locations, a profile of dissolved gas concentration along the length of the water source 302 can be determined.

Figure 4:
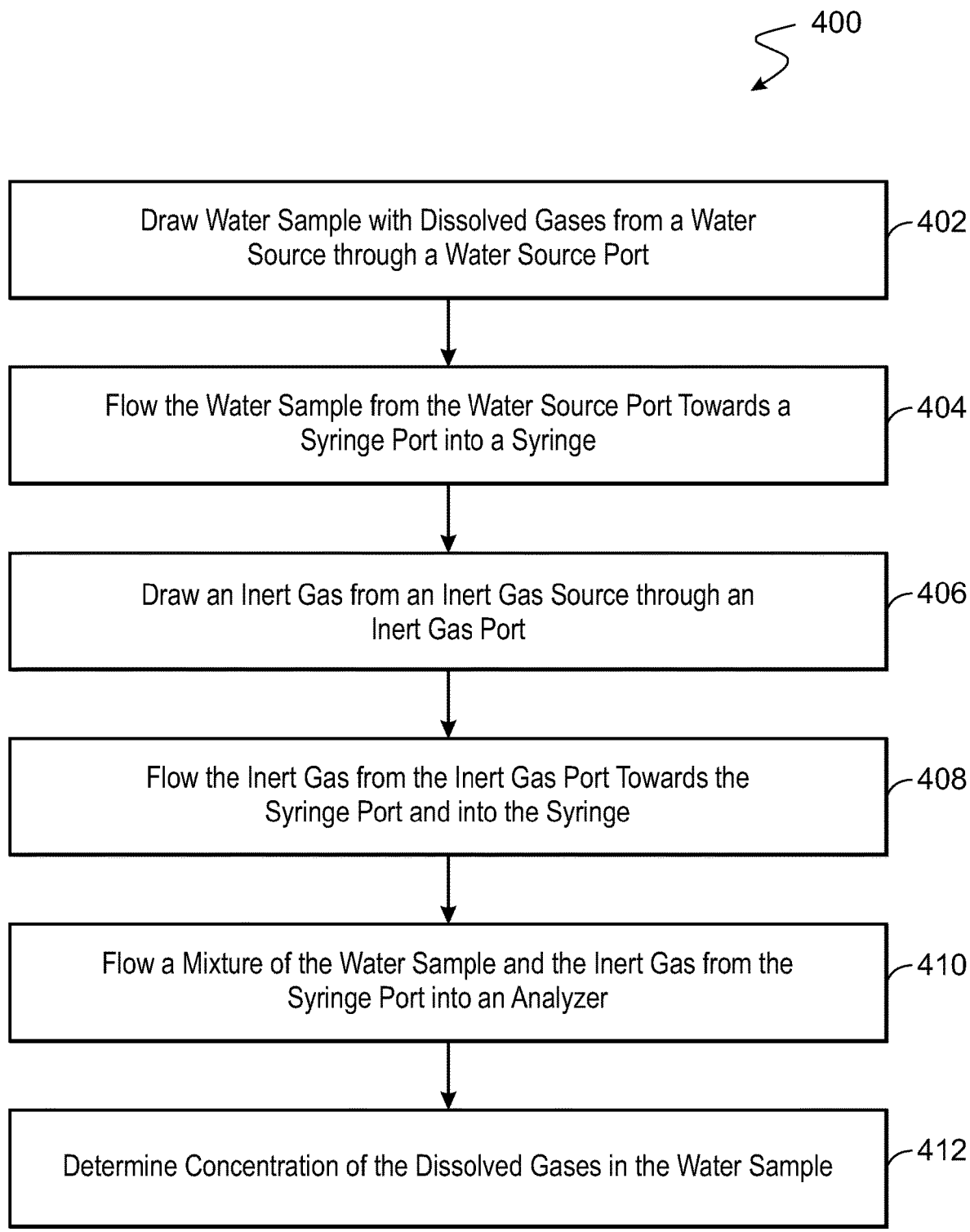
FIG. 4 is a flowchart of an example of a process to analyze concentration of dissolved gases in water.

FIG. 4 is a flowchart of an example of a process 400 to analyze the concentration of dissolved gases in water. In some implementations, the steps of the process 400 can be implemented by a controller that can transmit signals to control operations performed by components of systems described in this disclosure. In some implementations, at least some of the steps of the process 400 can be implemented manually by a user while other steps of the process 400 can be implemented by the controller. At step 402, a water sample with dissolved gases is drawn from a source carrying water with dissolved gases. The gases can be produced during oil and gas production or in other operations, such as sewage water treatment. The water sample is drawn to a water source port of a four-way valve. At step 404, the water sample is flowed from the water source port towards a syringe port and into a syringe that is fluidically coupled to the syringe port. The valve is set to avoid flow of the water sample to an inert gas port and an analyzer port of the valve. At step 406, inert gas is drawn from an inert gas source fluidically coupled to the inert gas port. At step 408, the inert gas is flowed from the inert gas port towards the syringe port and into the syringe. The valve is set to avoid flow of the inert gas to the water source port or the analyzer port. At step 410, a mixture of the water sample and the inert gas is flowed from the syringe port towards the analyzer port and into an analyzer fluidically coupled to the analyzer port. The valve is set to avoid flow of the mixture to the water source port or the inert gas port. At step 412, a concentration of the dissolved gases in the water sample is determined using the analyzer.

Thus, particular implementations of the subject matter have been described. Other implementations are within the scope of the following claims.

The invention claimed is:

1. A method comprising:
drawing, from a source carrying water with dissolved gases produced during oil and gas production, a water sample through a water source port of a four-way valve fluidically coupled to the water source;
flowing the water sample from the water source port towards a syringe port and into a syringe fluidically coupled to the syringe port, the syringe configured to hold the water sample, wherein flowing the water sample comprises avoiding an inert gas port and an analyzer port of the four-way valve;
drawing, from an inert gas source fluidically coupled to the inert gas port, inert gas;
flowing the inert gas from the inert gas port towards the syringe port and into the syringe, wherein flowing the inert gas comprises avoiding the water source port and the analyzer port; and
flowing a mixture of the water sample and the inert gas from the syringe port towards the analyzer port and into an analyzer fluidically coupled to the analyzer port, wherein flowing the mixture comprises avoiding the water source port and the inert gas port.

2. The method of claim 1, further comprising, after flowing the mixture of the water sample and the inert gas into the analyzer, determining, by the analyzer, a concentration of dissolved gases in the water sample using the mixture of the water sample and the inert gas.

3. The method of claim 2, wherein determining the concentration of dissolved gases comprises determining a mole fraction of each dissolved gas.

4. The method of claim 3, wherein the analyzer is a gas chromatography analyzer, wherein the method further comprises, before determining the concentration of dissolved gases in the water sample, calibrating the gas chromatography analyzer.

5. The method of claim 1, further comprising, after flowing the inert gas into the syringe and before flowing the mixture of the water sample and the inert gas into the analyzer, holding the mixture in the syringe for a duration to achieve gas equilibrium of the mixture in the syringe.

6. The method of claim 5, wherein the duration is between 45 minutes and one hour.

7. The method of claim 1, wherein the water with dissolved gases flows through the source at a temperature, wherein the method further comprises, before flowing the water sample into the syringe, heating the water sample to a temperature equal to the temperature at which the water with dissolved gases flows through the source.

8. The method of claim 1, wherein the method further comprises, before flowing the water sample into the syringe, filtering suspended solids in the water sample.

9. A system comprising:
a four-way valve comprising:
a syringe port fluidically coupled to a source carrying water with dissolved gases produced during oil and gas production,
a water source port fluidically coupled to a syringe configured to hold the water sample,
an inert gas port fluidically coupled to an inert gas source, and
an analyzer port;
a controller connected to the four-way valve, the controller comprising:

one or more computer systems, and a computer-readable medium storing instructions executable by the one or more computer systems to control the four-way valve to perform operations comprising:

drawing a water sample through the water source port, flowing the water sample from the water source port to the syringe port while avoiding the inert gas port and the analyzer port, wherein the water sample is flowed to the syringe, after the water sample is flowed to the syringe, drawing inert gas from the inert gas source and flowing the inert gas to the syringe port and into the syringe while avoiding the water source port and the analyzer port, and flowing a mixture of the water sample and the inert gas from the syringe port towards the analyzer port; and an analyzer fluidically coupled to the analyzer port, the analyzer configured to receive the mixture of the water sample and the inert gas and to determine a concentration of dissolved gases in the water sample using the mixture of the water sample and the inert gas.

10. The system of claim 9, wherein the analyzer is a gas chromatography analyzer.

11. The system of claim 10, wherein the gas chromatography analyzer is configured to determine a mole fraction of each dissolved gas.

12. The system of claim 9, wherein the water with dissolved gases flows through the source at a temperature, wherein the system further comprises a heater configured to heat the water sample to a temperature equal to the temperature at which the water with dissolved gases flows through the source.

13. The system of claim 9, further comprising a filter configured to filter suspended solids in the water sample before the water sample is flowed to the syringe.

14. The system of claim 9, wherein the inert gas is helium, wherein the system comprises a helium tank comprising helium and fluidically coupled to the inert gas port.

* * * * *